United States Patent [19]

Robertson

[11] 4,374,780

[45] Feb. 22, 1983

[54] DI-2,4,4'-TRIMETHYLPENTYLPHOSPHINIC ACID AND ITS PREPARATION

[75] Inventor: Allan J. Robertson, Niagara, Canada

[73] Assignee: American Cyanamid Company, Stamford, Conn.

[21] Appl. No.: 263,529

[22] Filed: May 14, 1981

[51] Int. Cl.$^3$ ............................................. C07F 9/30
[52] U.S. Cl. .............................. 260/502.4 R; 75/119; 210/634; 210/912; 423/139
[58] Field of Search .................. 260/502.4 R; 423/139

[56] References Cited

U.S. PATENT DOCUMENTS 2,957,931  10/1960  Hamilton et al. ............ 260/502.4 R
3,052,514  9/1962  Schmitt ........................ 260/502.4 R Primary Examiner—Joseph E. Evans
Attorney, Agent, or Firm—Michael J. Kelly

[57] ABSTRACT

Free radical addition of two moles of 2,4,4'-trimethylpentene-1 to 2,4,4'-trimethylpentylphosphine followed by the oxidation of the 2,4,4'-trimethylpentylphosphine with two moles of hydrogen peroxide is employed to prepare 2,4,4'-trimethylpentylphosphinic acid. The 2,4,4'-trimethylpentylphosphinic acid is useful as a cobalt extractant.

1 Claim, No Drawings

DI-2,4,4'-TRIMETHYLPENTYLPHOSPHINIC ACID AND ITS PREPARATION

The invention relates to di-2,4,4'-trimethylpentylphosphinic acid, i.e.

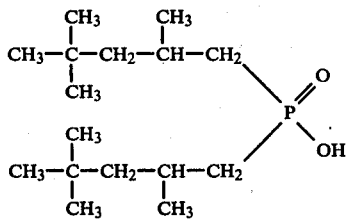

and a method for the production thereof which comprises free radical addition of two moles of 2,4,4'-trimethylpentene-1 to phosphine followed by oxidation with two moles of hydrogen peroxide. The end product, either as an acid or in its salt form, finds utility as a cobalt extractant and, more specifically, as a selective extractant for cobalt (II) in aqueous cobalt (II)-bearing solutions containing nickel (II).

In the preparation of this compound free radical initiators of the azobis type are preferred although others, such as the peroxides, may be used. Azobisisobutyrylnitrile is the most preferred. Pure 2,4,4'-trimethylpentene-1 is commercially available or may be prepared with diisobutylene. The temperature range of the reaction is directly related to the half life of the initiator employed. For azobisisobutyrylnitrile the temperature range should be from about 40°–110° C., preferably 60° to 90° C. The phosphine addition will take place at any temperature, however to reduce unwanted tri-2,4,4'-trimethylpentylphosphine, high phosphine pressures, i.e., high phosphine to olefin mole ratios, are required. The preferred range is 300–700 psig although pressure ranging from 0 to 1000 psig can be employed. Under high phosphine conditions the mono 2,4,4'-trimethylpentylphosphine formed can be recycled and converted into the di-form. Tri-2,4,4'-trimethylpentylphosphine formed under low phosphinic pressures is a yield loss.

In the oxidation stage, the oxidation of the dialkylphosphine to the dialkylphosphine oxide is exothermic and takes place readily at 30° C.–100° C., preferably for this first oxidation step at 50° C.–70° C. To convert the dialkylphosphine oxide to the dialkylphosphinic acid, the temperature should be increased to within 50° C. to 120° C., preferably 80° C. to 100° C. Higher temperatures tend to remove one alkyl group forming some monoalkylphosphonic acid. At lower temperatures the oxidation is rather slow and excessive reaction times may be required.

Whereas the exact scope of the instant invention is set forth in the appended claims, the following specific examples illustrate certain aspects of the present invention, and, more particularly, point out methods of evaluating the same. However, the examples are set forth for illustration only and are not to be construed as limitations on the present invention except as set forth in the appended claims. All parts and percentages are by weight unless otherwise specified.

EXAMPLE 1

1500 parts of diisobutylene (a commercial source of 2,4,4'-trimethylpentene-1 consisting of 70% 2,4,4'-trimethylpentene-1 and 30% 2,4,4'-trimethylpentene-2) is charged to the autoclave along with 25 parts azobis isobutyrylnitrile (Vazo 64 ®).

The autoclave is pressurized to 550 psig with phosphine and is quickly heated to 60° C. At this point the pressure begins to drop as the phosphine addition to 2,4,4'-trimethylpentene-1 begins. The pressure is maintained at 550 psig by the addition of more phosphine. The temperature is slowly raised from 60° C. to 90° C. over a 4½ hour period. A further ½ hour at 90°–100° C. destroys any remaining initiator and the reaction stops. The excess phosphine is vented off and the reaction product is cooled and discharged. A total of 546 parts of phosphine are used in the reaction. 1593 parts of product containing 15.62% 2,4,4'-trimethylpentene-1, 19.34% 2,4,4'-trimethylpentene-2, 34.63% mono 2,4,4'-trimethylpentylphosphine, 22.39% di-2,4,4'-trimethylpentylphosphine and 2.0% tri-2,4,4'-trimethylpentylphosphine are recovered.

The product mixture is distilled to recover the di-2,4,4'-trimethylpentylphosphine. The vapor temperature of the various components are as follows:

| olefin mixture | 90° C. (510 mm Hg) |
|---|---|
| mono 2,4,4'-trimethylpentylphosphine | 110° C. (124 mm Hg) |
| di-2,4,4'-trimethylpentylphosphine | 140° C. (64.5 mm Hg) |

477.1 parts of di-2,4,4'-trimethylpentylphosphine containing 0.27 mono and 2.44% tri-2,4,4'-trimethylpentylphosphine are charged to a heated stirred resin flask under an inert atmosphere. The dialkylphosphine is heated to 60° C. 290 parts of 22.49% H$_2$O$_2$ is added with stirring over a ¾ hour period at 60°–70° C. The remaining 290 parts are added over 1 hour period at 95°–98° C. The product separated as a clear oily layer on top of the aqueous phase.

The product is decanted from the aqueous phase and is vacuumed dried overnight at 60° C. A total of 520 parts are recovered. It assayed 88% di-2,4,4'-trimethylpentyl-phosphinic acid and had a pKa of 6.03±0.05 in 75% isopropanol.

The $^{31}$P NMR chemical shift of the 2,4,4'-trimethylpentylphosphinic acid in isopropanol is −53.68 ppm with respect to 85% H$_3$PO$_4$. The $^{31}$P NMR spectrum also indicated the presence of 2.0% di-2,4,4'-trimethylpentylphosphine oxide, 4.0% tri-2,4,4'-trimethylpentylphosphine oxide and 7–8% total of 4 different phosphonic acids or phosphonate esters.

EXAMPLE 2

The following example illustrates the ability of di-2,4,4'-trimethylpentylphosphinic acid to separate cobalt (II) from nickel (II).

The di-2,4,4'-trimethylpentylphosphinic acid is dissolved in an aliphatic petroleum diluent (Solvesso ® 100) modified with 5% v/v isodecanol to obtain a concentration of 15% by volume, then a predetermined amount of 28% ammonium hydroxide is added to adjust the pH. An aliquot (50 mls.) is shaken at 50° C. for 10 minutes at 50° C. with an equal volume of an aqueous solution containing 1.97 gpl of cobalt (II) and 93.6 gpl of nickel (II), respectively, as sulfate salts, to extract the cobalt (II) into the organic phase. The aqueous phase is then separated from the organic phase and analyzed for cobalt (II) content. Based on the results obtained, the percent cobalt (II) extracted is calculated by mass balance. The percent nickel (II) extracted is determined by analyzing the organic phase. The results obtained are shown in Table I.

TABLE I

| % Metal Extraction | | Co/Ni Separation Factor[1] | Equilibrium pH |
| --- | --- | --- | --- |
| Co | Ni | | |
| 3.09 | 0 | — | 2.81 |
| 38.2 | 0.28 | 217 | 3.99 |
| 85.1 | 1.10 | 516 | 4.94 |
| 97.8 | 2.22 | 1975 | 5.33 |
| 100 | 3.10 | — | 5.52 |

[1] Separation factor $= \dfrac{E^\circ_A \, Co\,(II)}{E^\circ_A \, Ni\,(II)}$, where $E^\circ_A = \dfrac{\text{equilibrium concentration of the metal in the organic phase}}{\text{equilibrium concentration of the metal in the aqueous phase}}$

EXAMPLE 3

The procedure of Example 1 is followed except that a solution of 180 gpl of the di-2,4,4'-trimethylpentylphosphinic acid in Varsol DX-3641 modified with 5% v/v isodecanol is used. The initial sulphate solution contained 1.90 gpl Co and 103.6 gpl Ni. The A/O ratio is 1.0 and the temperature is maintained at 50° C. for a 10-minute contact. Test results are set forth in Table II.

TABLE II

| % Metal Extraction | | Co/Ni Separation Factor | Equilibrium pH |
| --- | --- | --- | --- |
| Co | Ni | | |
| 3.1 | 0 | — | 2.63 |
| 29.5 | 0.89 | — | 3.62 |
| 57.6 | 0.99 | 135 | 4.30 |
| 83.5 | 1.63 | 305 | 4.89 |
| 88.5 | 1.93 | 391 | 5.00 |
| 91.2 | 2.48 | 407 | 5.12 |

I claim:
1. The compound di-2,4,4'-trimethylpentylphosphinic acid.

* * * * *